United States Patent
Chen et al.

(10) Patent No.: US 6,675,032 B2
(45) Date of Patent: *Jan. 6, 2004

(54) VIDEO-BASED SURGICAL TARGETING SYSTEM

(75) Inventors: David T. Chen, Somerville, MA (US); Steven D. Pieper, Thetford Center, VT (US); Michael A. McKenna, Cambridge, MA (US)

(73) Assignee: Medical Media Systems, West Lebanon, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/746,992

(22) Filed: Dec. 21, 2000

(65) Prior Publication Data

US 2003/0032876 A1 Feb. 13, 2003

Related U.S. Application Data

(63) Continuation of application No. 09/098,159, filed on Jun. 16, 1998, now abandoned, which is a continuation of application No. 08/320,502, filed on Oct. 7, 1994, now Pat. No. 5,765,561.

(51) Int. Cl.$^7$ ................................................. A61B 5/05
(52) U.S. Cl. ........................ 600/407; 128/920; 128/922
(58) Field of Search ............................ 600/407; 348/77; 128/920, 922

(56) References Cited

U.S. PATENT DOCUMENTS

| | | |
|---|---|---|
| 4,722,056 A | 1/1988 | Roberts et al. |
| 4,729,098 A | 3/1988 | Cline et al. |
| 4,882,679 A | 11/1989 | Tuy et al. |
| 4,922,909 A | 5/1990 | Little et al. |
| 4,945,478 A | 7/1990 | Merickel et al. |
| 4,965,844 A | 10/1990 | Oka et al. |
| 4,985,855 A | 1/1991 | Aldrich et al. |
| 4,989,083 A | 1/1991 | Eino |
| 5,005,559 A | 4/1991 | Blanco et al. |
| 5,151,856 A | 9/1992 | Halmann et al. |
| 5,153,721 A | 10/1992 | Eino et al. |
| 5,179,638 A | 1/1993 | Dawson et al. |
| 5,230,623 A | 7/1993 | Guthrie et al. |
| 5,231,483 A | 7/1993 | Sieber et al. |
| 5,255,352 A | 10/1993 | Falk |
| 5,261,404 A | 11/1993 | Mick et al. |

(List continued on next page.)

OTHER PUBLICATIONS

Vanroden, "Don't Look Now, But A Body Has Been Found In The Basement Of Cummings Hall", Dartmouth Thayer School of Engineering Directions, a periodical published by the Trustees of Dartmouth College, Hanover, New Hampshire, vol. 8, No. 1, Fall 1993, pp. 30–36.

Roberts et al., "A frameless stereotaxic integration of computerized tomographic imaging and the operating microscope", J. Neurosurg.—vol. 65—Oct. 1986, pp. 545–549.

Weisburn et al., "An interactive graphics editor for 3D surgical simulation", SPIE vol. 626 Medicine XIV–Pacs IV (1986), pp. 483–490.

Shalev et al., "Pseudo–3D imaging with the DICOM–8", SPIE vol. 555 Medical Imaging and Instrumentation '85 (1985), pp. 63–66.

Applicants'"IRA Magaziner Demo (SEETM)", displayed 6–93 (23 minutes).

Fowler, "Computers May Drive Revolution in Neurosurgery Techniques", Washington Post, Science, Aug. 15, 1994.

Kawata et al., "Three–Dimensional Imaging of Blood Vessels Using Cone–Beam CT", IEEE Comput. Soc. Press, Proceedings ICIP–94, vol. 2, pp. 140–144.

(List continued on next page.)

Primary Examiner—Francis J. Jaworski
Assistant Examiner—Runa S. Qaderi
(74) Attorney, Agent, or Firm—Pandiscio & Pandiscio

(57) ABSTRACT

A video-based surgical targeting system for targeting anatomical structures within a patient.

25 Claims, 7 Drawing Sheets

U.S. PATENT DOCUMENTS

| | | |
|---|---|---|
| 5,274,551 A | 12/1993 | Corby, Jr. |
| 5,291,889 A | 3/1994 | Kenet et al. |
| 5,295,199 A | 3/1994 | Shino |
| 5,297,215 A | 3/1994 | Yamagishi |
| 5,319,551 A | 6/1994 | Sekiguchi et al. |
| 5,329,310 A | 7/1994 | Liljegren et al. |
| 5,363,476 A | 11/1994 | Kurashige et al. |
| 5,378,915 A | 1/1995 | Hines et al. |
| 5,383,454 A | 1/1995 | Bucholz |
| 5,384,594 A | 1/1995 | Sieber et al. |
| 5,398,684 A | 3/1995 | Hardy |
| 5,417,210 A | 5/1995 | Funda et al. |
| 5,447,154 A | 9/1995 | Cinquin et al. |
| 5,448,687 A | 9/1995 | Hoogerhyde et al. |
| 5,461,706 A | 10/1995 | Trow et al. |
| 5,491,510 A | 2/1996 | Gove |
| 5,493,595 A | 2/1996 | Schoolman |
| 5,497,452 A | 3/1996 | Shimizu et al. |
| 5,511,153 A | 4/1996 | Azarbayejani et al. |
| 5,526,812 A | 6/1996 | Dumoulin et al. |
| 5,526,814 A | 6/1996 | Cline et al. |
| 5,531,227 A | 7/1996 | Schneider |
| 5,537,638 A | 7/1996 | Morita et al. |
| 5,558,619 A | 9/1996 | Kami et al. |

OTHER PUBLICATIONS

Klein et al., "Identifying Vascular Features With Orientation Specific Filters And B–Spine Snakes", IEEE Comput. Soc. Press, Computers in Cardiology 1994, pp. 113–116.

Chen et al., "Left Ventricle Global Motion And Shape From CT Volumetric Data", IEEE Apr. 1993, pp. V–101 to V–104 (reprint).

VIDEO-BASED SURGICAL TARGETING SYSTEM

This application is a Continuation of U.S. Ser. No. 09/098,159, filed Jun. 16, 1998, abandoned, which is a Continuation of U.S. Ser. No. 08/320,502, filed Oct. 7, 1994, now U.S. Pat. No. 5,765,561.

FIELD OF THE INVENTION

This invention relates to surgical systems in general, and more particularly to surgical targeting systems.

BACKGROUND OF THE INVENTION

Many medical procedures must be carried out at an interior site which is normally hidden from the view of the physician. In these situations, the physician typically uses some sort of scanning device to examine the patient's anatomy at the interior site prior to, and in preparation for, conducting the actual procedure itself. These scanning devices typically include MRI devices, CT scanners, X-ray machines, ultrasound devices and the like, and serve to provide the physician with a preliminary knowledge of the patient's internal anatomical structure prior to commencing the procedure. The physician can then use this information to plan the procedure in advance, taking into account patient-specific anatomical structure. In addition, the physician can also use the information obtained from these scans to more precisely identify the location of selected structures (e.g. tumors and the like) which may themselves be located within internal organs or other internal body structures. As a result, the physician can more easily "zero in" on such selected structures during the subsequent procedure, with less trauma to host organs or other internal body structures. Furthermore, in many cases the structures of interest may be quite small and difficult to identify with the naked eye. In these cases, preliminary scanning of the patient's internal anatomy using high resolution scanning devices can help the physician locate such structures during the subsequent procedure.

In general, scanning devices of the sort described above tend to generate a series of two-dimensional (i.e., "2-D") images of the patient's anatomical structure. For example, CT scanners generate 2-D images which are viewed directly by the physician. By viewing a plurality of these 2-D images, the physician can mentally generate a three-dimensional (i.e., "3-D") sense of the patient's anatomical structure.

Some scanning devices create large numbers of 2-D images during the scanning process, with each 2-D image representing a plane or slice taken through the scanned structure. Furthermore, some scanning devices also have associated computer hardware and software for building a 3-D computer model of the patient's scanned structure using a plurality of these 2-D images. For example, some MRI devices and some CT scanners have such associated computer hardware and software. In these cases, an operator using this scanning equipment and associated computer hardware and software can create a number of 2-D images, assemble them into a 3-D computer model of the scanned structure, and then generate various images of that 3-D computer model as seen from various angles so as to enhance understanding of the patient's anatomical structure.

While the information generated by the aforementioned scanning devices is generally of great benefit to physicians, certain significant limitations still exist. For one thing, it can be very difficult for a physician to physically locate a particular anatomical structure during a medical procedure, even when that structure is readily identifiable in a scanned image. This may be because the structure is very small and difficult to see with the naked eye, or because it is not readily visible against a particular background, or because it is itself located within an internal organ or other internal body structure, etc. For another thing, even when the structure of interest is successfully located by the physician, it can sometimes still be extremely difficult for the physician to reliably direct a medical instrument to that structure. This may be because the structure is quite small and difficult to target accurately, or because intervening body structure mandates a complex approach, etc.

OBJECTS OF THE INVENTION

Accordingly, one object of the present invention is to provide a surgical targeting system to facilitate locating a particular anatomical structure during a medical procedure.

Another object of the present invention is to provide a video-based surgical targeting system to facilitate locating a particular anatomical structure during a medical procedure.

And another object of the present invention is to provide a video-based surgical targeting system which permits a series of patient-specific 2-D images (obtained by scanning patient anatomy using one or more scanning devices of the type described above) to be assembled into a 3-D computer model of the patient's scanned structure.

Still another object of the present invention is to provide a video-based surgical targeting system which allows a physician to view the aforementioned patient-specific 2-D images on a display in any desired access sequence.

And another object of the present invention is to provide a video-based surgical targeting system which allows a physician to assemble a series of patient-specific 2-D images into a patient-specific database, and then to generate virtual images from the aforementioned patient-specific database, as seen from any desired virtual camera position, for viewing on a display.

Yet another object of the present invention is to provide a video-based surgical targeting system which allows a physician to generate virtual images from the aforementioned 3-D computer model, as seen from any desired virtual camera position, for viewing on a display.

And another object of the present invention is to provide a video-based surgical targeting system which permits a physician to place virtual planning markers about any sites of interest while viewing one or more of the aforementioned patient-specific 2-D images, with those virtual planning markers then being incorporated into the 3-D computer model, whereby those virtual planning markers can be displayed in their appropriate 3-D positions when generating virtual images of the 3-D computer model.

Still another object of the present invention is to provide a video-based surgical targeting system which permits a physician to place virtual planning markers about any sites of interest while viewing virtual images of the 3-D computer model, with those virtual planning markers then being incorporated into the 3-D computer model, whereby those virtual planning markers can be displayed in their appropriate positions when generating subsequent virtual images of the 3-D computer model.

Still another object of the present invention is to provide a video-based surgical targeting system which permits a physician to place virtual planning markers about any sites of interest while viewing virtual images of the 3-D computer model, with those virtual planning markers then being incorporated into the 3-D computer model and into the database of 2-D images, whereby those virtual planning markers can be displayed in their appropriate positions when subsequently generating virtual images of the 3-D computer model or when subsequently displaying 2-D images from the patient-specific database.

Yet another object of the present invention is to provide a video-based surgical targeting system which permits a real image obtained by a real-time imaging device (e.g. a video camera) to be displayed to a physician, and which permits a virtual image generated from the 3-D computer model to be displayed to a physician, according to the directive of the physician.

Another object of the present invention is to provide a video-based surgical targeting system which permits a real image obtained by a real-time imaging device (e.g. a video camera) to be appropriately merged with a corresponding virtual image generated from the 3-D computer model.

And another object of the present invention is to provide a video-based surgical targeting system which permits a real image obtained by a real-time imaging device (e.g. a video camera) to be appropriately merged with a corresponding virtual image generated from the 3-D computer model, whereby the two images will be in registration with one another.

Still another object of the present invention is to provide a video-based surgical targeting system which permits a real image obtained by a real-time imaging device (e.g. a video camera) to be merged with a corresponding virtual image generated from the 3-D computer model, whereby the two images will be in registration with one another, and whereby the physician can choose to display either one of the two images exclusive of the other, or a composite of both images simultaneously.

Yet another object of the present invention is to provide a video-based surgical targeting system which permits a real image obtained by a real-time imaging device (e.g. a video camera) to be merged with a corresponding virtual image generated from the 3-D computer model, whereby the two images will be simultaneously displayed in registration with one another, and whereby the physician can modify the virtual image generated from the 3-D computer model as needed, by clipping or fading, so as to expose the virtual planning markers to view, with the virtual planning markers being superimposed on the real image generated by the real-time viewing device.

And another object of the present invention is to provide a video-based surgical targeting system which permits a real image generated by a real-time imaging device (e.g. a video camera) to be merged with a corresponding virtual image generated from the 3-D computer model, whereby the two images will be simultaneously displayed in registration with one another, and whereby the physician can modify the virtual image generated from the 3-D computer model so as to expose only the virtual planning markers to view, with the virtual planning markers being superimposed on the real image generated by the real-time imaging device.

Still another object of the present invention is to provide a video-based surgical targeting system which permits a real image obtained by a real-time imaging device (e.g. a video camera) to be merged with a corresponding virtual image generated from the 3-D computer model, whereby the two images will be simultaneously displayed in registration with one another, and whereby this registration will be automatically maintained even as the real-time imaging device is moved about relative to the anatomical site, with the virtual image being automatically generated so as to follow the real image.

Still another object of the present invention is to provide a video-based surgical targeting system which permits a real image obtained by a real-time imaging device (e.g. a video camera) to be merged with a corresponding virtual image generated from the 3-D computer model, whereby the two images will be simultaneously displayed in registration with one another, and whereby this registration will be automatically maintained through the use of a computerized position and orientation tracker connected to the imaging device even as the real-time imaging device is moved about relative to the anatomical site, with the virtual image being automatically generated so as to follow the real image.

Still another object of the present invention is to provide a video-based surgical targeting system which permits a real image obtained by a real-time imaging device (e.g. a video camera) to be merged with a corresponding virtual image generated from the 3-D computer model, whereby the two images will be simultaneously displayed in registration with one another, and whereby this registration will be automatically maintained through the use of a computer search algorithm based on the real image and the virtual image even as the real-time imaging device is moved about relative to the anatomical site, with the virtual image being automatically generated so as to follow the real image.

Yet another object of the present invention is to provide a video-based surgical targeting system which permits a real image obtained by a real-time imaging device (e.g. a video camera) to be merged with a corresponding virtual image generated from the 3-D computer model, whereby the two images will be simultaneously displayed in registration with one another, and whereby a surgical instrument can be tracked along with the real-time imaging device in order that the surgical instrument can be guided about the anatomical site using the virtual image generated from the 3-D computer model.

And another object of the present invention is to provide a video-based surgical targeting system which permits a virtual image to be generated from the 3-D computer model, and further wherein this virtual image can correspond to an "over the shoulder" view of the working tip of a surgical instrument located at the anatomical site.

And another object of the present invention is to provide an improved method for locating anatomical structures during a medical procedure.

SUMMARY OF THE INVENTION

These and other objects of the present invention are achieved through the provision and use of a novel video-based surgical targeting system.

In one form of the invention, the video-based surgical targeting system comprises a patient-specific database comprising a plurality of 2-D images of the anatomical structure of a patient; a patient-specific 3-D computer model of the anatomical structure of the patient, the patient-specific 3-D computer model being assembled from the plurality of 2-D images contained in the patient-specific database; marker placement means for (i) inserting virtual planning markers into the 2-D images contained in the patient-specific database, and/or (ii) adjusting the positions of virtual planning markers inserted into the 2-D images contained in the patient-specific database and thereafter incorporated into the patient-specific 3-D computer model, or inserting virtual planning markers into the 3-D computer model; an image generator for generating a virtual image of the anatomical structure modeled by the patient-specific 3-D computer model; real-time image generating means for generating a real image of the anatomical structure of a patient; video mixing means for mixing the virtual image and the real image into an output image, whereby the output image may comprise either one of the two images exclusive of the other, or a composite of both images; and display means for displaying the output image.

Preferably the video-based surgical targeting system also includes registration means for placing the virtual image in registration with the real image. These registration means may include means for manually aligning the virtual image with the real image, or means for automatically aligning the virtual image with the real image. The registration means may also include tracking means for tracking the position of the real-time image generating means.

Preferably, the video-based surgical targeting system further comprises instrument tracking means for tracking the position of a surgical instrument.

In an alternative form of the invention, the video-based surgical targeting system comprises a patient-specific database comprising a plurality of 2-D images of the anatomical structure of a patient; marker placement means for inserting virtual planning markers into the 2-D images contained in the patient-specific database; an image generator for generating a virtual image of the anatomical structure represented by the plurality of 2-D images contained in the patient-specific database; real-time image generating means for generating a real image of the anatomical structure of a patient; video mixing means for mixing the virtual image and the real image into an output image, whereby the output image may comprise either one of the two images exclusive of the other, or a composite of both images; and display means for displaying the output image.

In another alternative form of the invention, the video-based surgical targeting system comprises a patient-specific database comprising a plurality of images of the anatomical structure of a patient; a patient-specific 3-D computer model of the anatomical structure of the patient, the patient-specific 3-D computer model being assembled from the plurality of images contained in the patient-specific database; marker placement means for (i) inserting virtual planning markers into the images contained in the patient-specific database, and/or (ii) adjusting the positions of virtual planning markers inserted into the images contained in the patient-specific database and thereafter incorporated into the patient-specific 3-D computer model, or inserting virtual planning markers into the 3-D computer model; an image generator for generating a virtual image of the anatomical structure modeled by the patient-specific 3-D computer model; real-time image generating means for generating a real image of the anatomical structure of a patient; video mixing means for mixing the virtual image and the real image into an output image, whereby the output image may comprise either one of the two images exclusive of the other, or a composite of both images; and display means for displaying said output image.

In yet another alternative form of the invention, the video-based surgical targeting system comprises a patient-specific database comprising a plurality of 2-D images of the anatomical structure of a patient; marker placement means for inserting virtual planning markers into the 2-D images contained in the patient-specific database; an image generator for generating a virtual image of the anatomical structure defined by the patient-specific database; real-time image generating means for generating a real image of the anatomical structure of a patient, the real-time image generating means being adapted so as to dynamically update the patient-specific database via the real image; video mixing means for mixing the virtual image and the real image into an output image, whereby the output image may comprise either one of the two images exclusive of the other, or a composite of both images; and display means for displaying said output image.

The present invention also comprises a method for targeting an anatomical structure using the video-based surgical targeting system.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein.

DETAILED DESCRIPTION OF THE PREFERRED EMBODIMENTS

Figure 1:
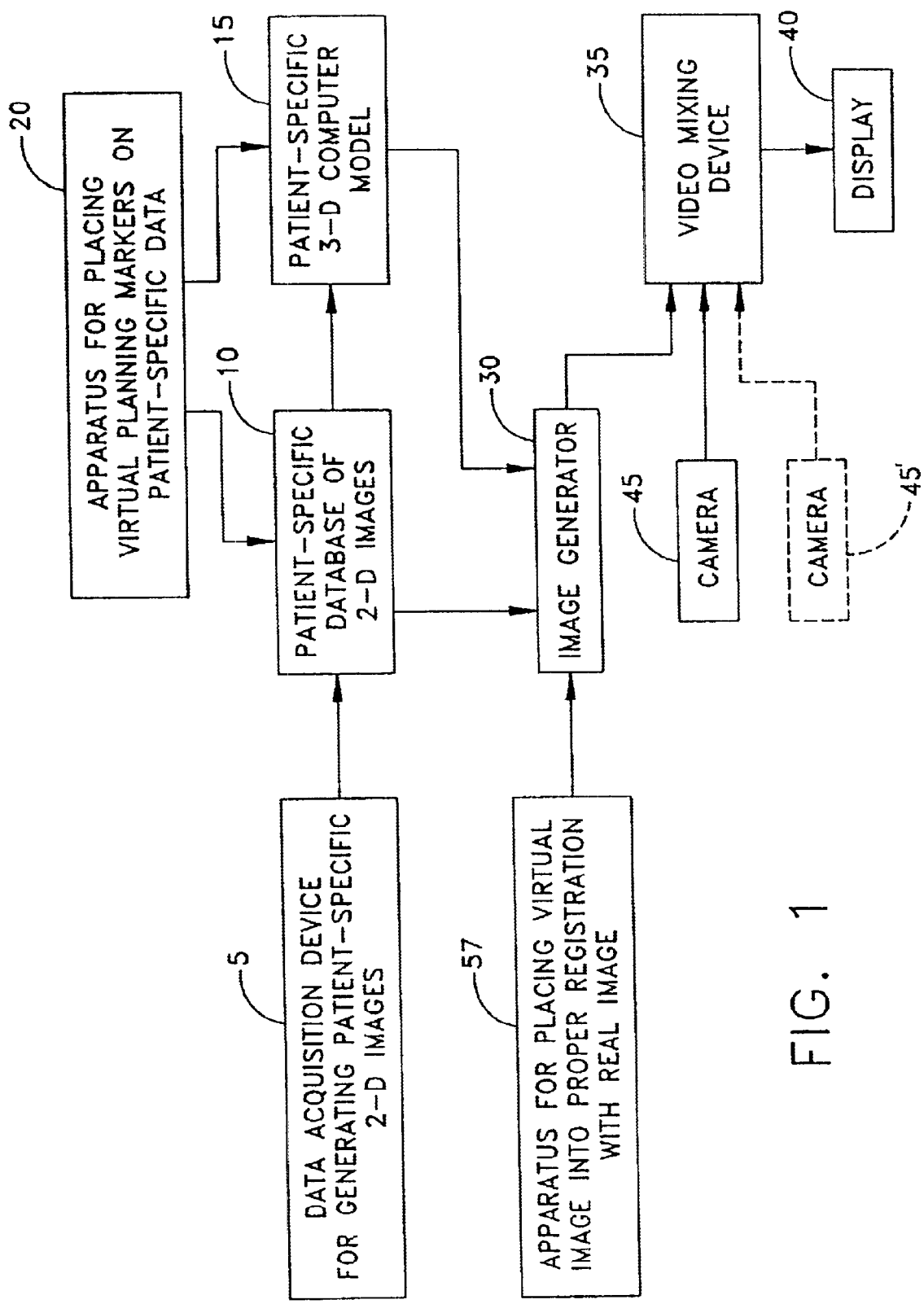
FIG. 1 is a schematic view of the major components of a video-based surgical targeting system formed in accordance with the present invention.

Looking first at FIG. 1, the starting point for the present invention involves a data acquisition device 5 which is adapted to generate patient-specific 2-D images. For example, data acquisition device 5 might comprise an MRI device, a CT scanner or any other scanning device of the sort adapted to provide a series of 2-D images of the patient's anatomical structure, where each 2-D image corresponds to a plane or slice taken through the scanned structure. Alternatively, data acquisition device 5 might comprise an X-ray machine or other imaging machine adapted to provide a set of 2-D images of the patient's anatomical structure, where each 2-D image corresponds to a data set relating to the scanned structure.

The patient-specific 2-D images generated by data acquisition device 5 are stored in a patient-specific database 10. Patient-specific database 10 is constructed so that the patient-specific 2-D images can be accessed individually or in any particular sequence desired. Preferably patient-specific database 10 comprises an appropriate set of data contained in a computer storage system.

The patient-specific 2-D images stored in patient-specific database 10 are used in building a patient-specific 3-D computer model 15. Patient-specific 3-D computer model 15 may be built from the information stored in patient-specific database 10 using any one of the many algorithms well known in the art, so long as the patient-specific 3-D computer model is capable of generating virtual images of the patient's anatomical structure from substantially any location where a real camera may be positioned relative to that anatomical structure during a given procedure. Alternatively, patient-specific 3-D computer model 15 may be built from the information stored in patient-specific database 10 using any one of die many algorithms well known in the art, where the patient-specific 3-D computer model is capable of generating virtual images of the patient's anatomical structure from a predetermined set of possible virtual camera positions. Preferably, patient-specific 3-D computer model 15 is constructed so that it is capable of generating virtual images of the patient's anatomical structure from any location whatsoever, with any desired field of view, and including any other camera-specific criteria desired (e.g. particular camera characteristics such as focus, optical characteristics, optical distortions, etc.). By way of example, one possible algorithm for building the patient-specific 3-D computer model out of the information stored in the patient-specific database 10 might be the Marching Cubes algorithm.

In one preferred embodiment of the invention, patient-specific 3-D computer model 15 comprises an appropriate computer software model resident on an appropriate digital computer. Patient-specific 3-D computer model 15 is preferably constructed using a plurality of polygonal models to model the patient's real anatomical structure. As is well known in the art, such polygonal models generally comprise a collection of points defining the surface of the 3-D computer model, along with some connectivity information relating to how these surface points are connected to one another. Preferably there is one polygonal model per anatomical structure being modeled. Of course, the choice of which particular computer software model is used to model a particular anatomical structure ultimately depends on a variety of factors, such as the particular anatomical structure being modeled, the computer hardware available, the volume of data to be handled, the particular medical procedure which is to be conducted, etc.

Of course, it is also anticipated that the patient-specific 3-D computer model could be dynamic as well as static. For example, dynamic changes could occur in the model as a result of computer simulation (e.g. through the use of a Finite Element Model) or because more current real-time data (e.g. from video camera 45) is used to update the model, or both.

It is also anticipated that patient-specific 3-D computer model 15 might include data from sources other than the 2-D images contained in patient-specific database 10. For example, patient-specific 3-D computer model 15 might include information obtained from a 3-D surface digitizer such as that used in certain types of cranial surgery, or patient-specific 3-D computer model 15 might include information obtained from a temperature probe or a chemical probe. In fact, in addition to the 2-D image data obtained from patient-specific database 10, patient-specific 3-D computer model 15 might include substantially any type of information gathered by almost any type of device or sensor or process.

An integral part of the present invention involves the placement of virtual planning markers into the patient-specific data, using apparatus 20. This may be done by placing such virtual planning markers into one or more of the patient-specific 2-D images contained in patient-specific database 10 before patient-specific 3-D computer model 15 is created; or by placing such virtual planning markers into patient-specific 3-D computer model 15 after that model has been created; or by some combination of the two.

Figure 3:
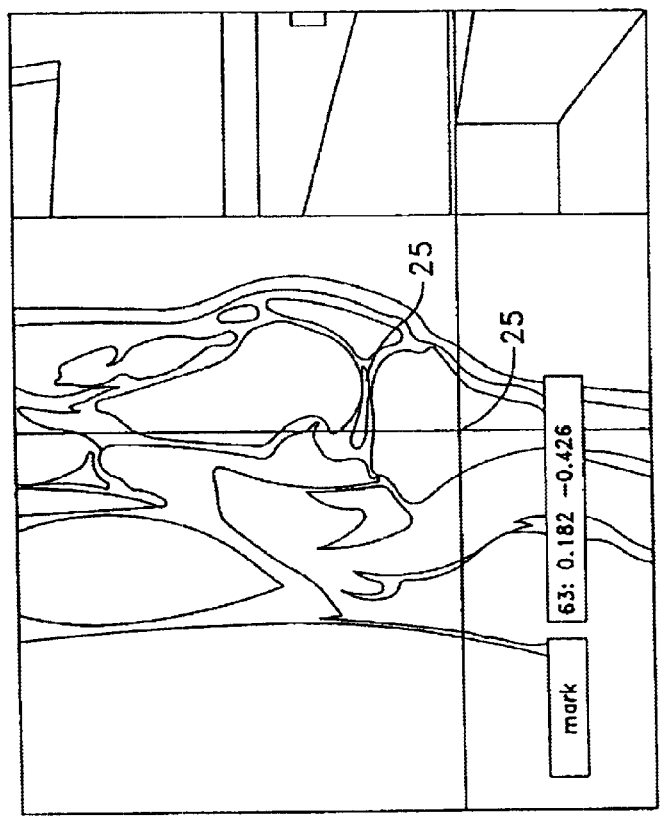
FIG. 3 is a view of an exemplary patient-specific 2-D image of the sort contained in the patient-specific database, wherein the image has had several virtual planning markers placed into the image.
Figure 2:
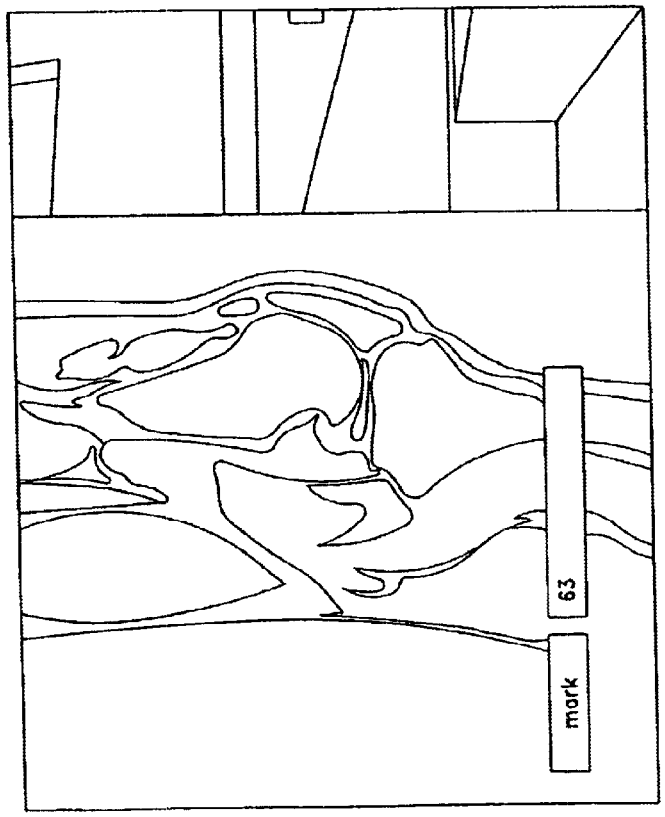
FIG. 2 is a view of an exemplary patient-specific 2-D image of the sort contained in the patient-specific database.

More particularly, apparatus 20 preferably comprises computer hardware and software adapted to allow a physician to access one or more of the patient-specific 2-D images contained in patient-specific database 10 aid present them for viewing, in tie manner shown in FIG. 2. Then, using a mouse or other data entry device, the physician can place one or more virtual planning markers 25 into an accessed patient-specific 2-D image, in the manner shown in FIG. 3. These virtual planning markers 25 can consist of substantially any geometric form such as a point, a line, a circle, a plane, a path (either straight or curved), etc., and are positioned about anatomical structures of particular interest to the physician. For example, virtual planning markers 25 might be placed about a suspected tumor, or they might be placed about particularly sensitive anatomical structures such as vascular tissue or nerve bundles, etc. Naturally, the particular geometric form chosen for a particular virtual planning marker may depend on a variety of factors, such as the particular anatomical structure involved, the computer hardware available, the volume of data to be handled, the particular medical procedure to be conducted, etc. Regardless of the particular form of virtual planning marker chosen, each virtual planning marker 25 which is placed on the 2-D image using apparatus 20 is then stored in patient-specific database 10 along with its associated 2-D image. As a result, when patient-specific 3-D computer model 15 is subsequently created from the data contained in patient-specific database 10, patient-specific 3-D computer model 15 will incorporate virtual planning markers 25 into the model.

Alternatively, a physician may use apparatus 20 to access patient-specific 3-D computer model 15 and then, using a mouse or other data entry device, adjust the position of one or more of the virtual planning markers 25 which were previously placed into patient-specific database 10 (and thus incorporated into patient-specific 3-D computer model 15 when that 3-D computer model was created). The adjusted positions of these virtual planning markers 25 are then stored in patient-specific 3-D computer model 15. Furthermore, an updated 2-D image of these virtual planning markers can then be incorporated into the patient-specific database 10.

Furthermore, where patient-specific 3-D computer model 15 has not already had a particular virtual planning marker 25 incorporated therein, a physician may also use apparatus 20 to access patient-specific 3-D computer model 15, and then use a mouse or other data entry device to insert one or more virtual planning markers 25 directly into patient-specific 3-D computer model 15.

Once virtual planning markers 25 have been properly positioned in patient-specific 3-D computer model 15, virtual images incorporating these virtual planning markers can be created by an image generator 30, fed through a video mixing device 35, and then presented to the physician on display 40.

At the same time, real images obtained from a video camera 45 can be fed through video mixing device 35 and then presented to the physician on display 40.

More particularly, image generator 30 comprises computer hardware and software of the sort well known in the art for generating virtual images from patient-specific 3-D computer model 15.

Video mixing device 35 comprises a video mixing device of the sort well known in the art, whereby the surgeon can selectively display (i) a virtual image created by image generator 30 from patient-specific 3-D computer model 15, (ii) a real image obtained from video camera 45, or (iii) a composite of the virtual image and the real image, where the virtual image is superimposed against the real image.

In order for the foregoing composite image to be more useful to the physician, the virtual image generated from patient-specific 3-D computer model 15 should be placed into registration with the real image obtained from video camera 45. This is done in several steps.

Figure 4:
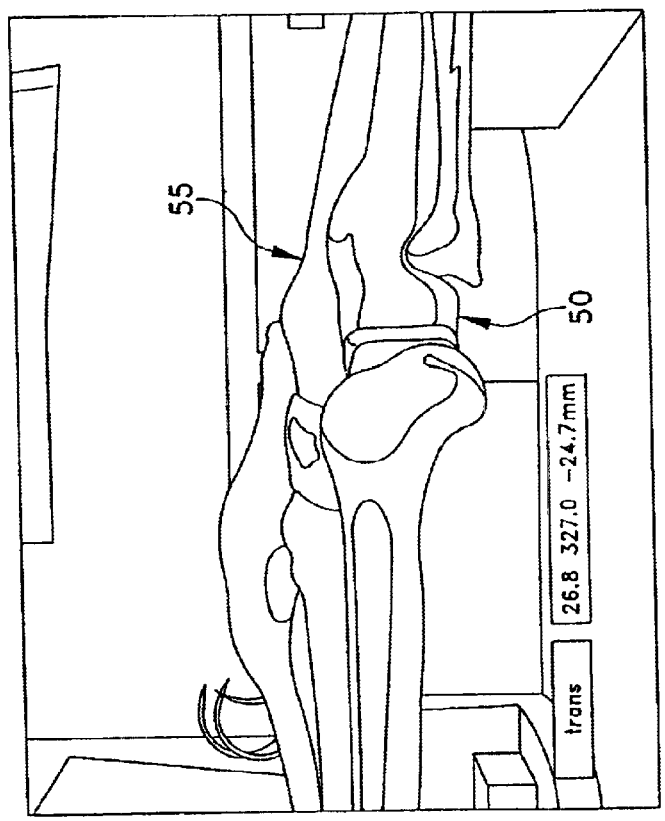
FIG. 4 is a composite view of (i) a real image obtained by a real-time imaging device (e.g. a video camera), and (ii) a virtual image generated from the 3-D computer model, wherein the two images are not yet in registration with one another.

First, and looking now at FIG. 4, a virtual image 50 is created by image generator 30, fed through video mixing device 35, and presented on display 40. Simultaneously, a real image 55 is captured by video camera 45, fed through video mixing device 35, and presented on display 40. Video mixing device 35 is arranged so as to present virtual image 50 and real image 55 simultaneously on display 40, with the virtual image being superimposed on the real image (i.e., so that the virtual image is in the foreground and the real image is in the background, in the manner shown in FIG. 4).

Figure 5:
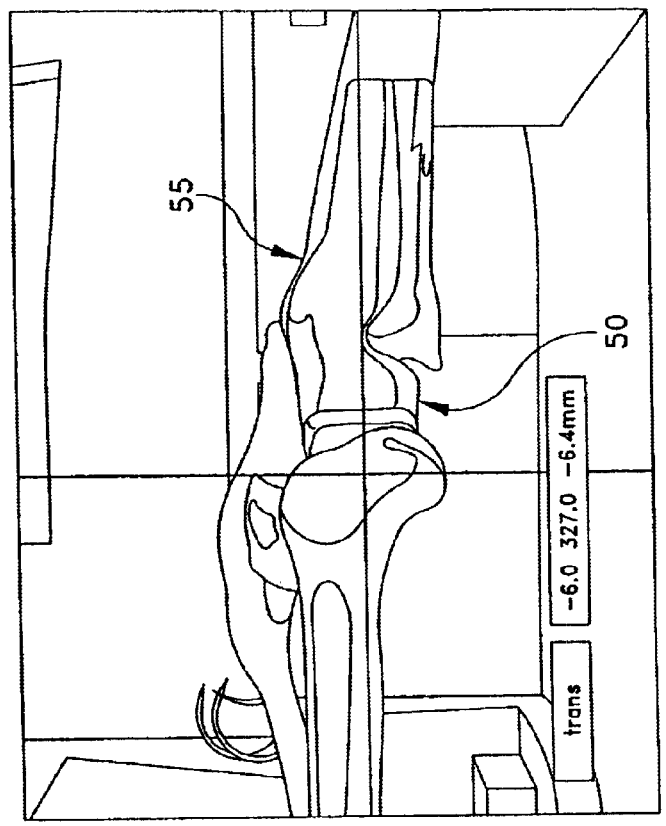
FIG. 5 is a composite view of (i) a real image obtained by a real-time imaging device (e.g. a video camera), and (ii) a virtual image generated from the 3-D computer model, wherein the two images have been placed in registration with one another.

Second, and looking now at FIG. 5, the two images are placed into proper registration with one another. This image registration can be accomplished in either one of two ways.

A first, and generally more preferable, technique involves holding the position of video camera 45 (and hence real image 55) constant and moving the position of the "virtual object" or the "virtual camera" by means of apparatus 57 until the virtual image 50 is brought into registration with real image 55. This can be done automatically by having image generator 30 use a search algorithm to match the virtual image to the real image, in which case apparatus 57 includes computer hardware and software of the sort well known in the art to cause image generator 30 to work through a search algorithm to match the virtual image to the real image; or it can be done manually, in which case apparatus 57 includes computer hardware and software of the sort well known in the art to allow the physician to drag the virtual image 50 into registration with real image 55, using a mouse or other data entry device attached to image generator 30. One convenient way that mouse motion can be used to control the 3-D movements of the patient-specific model is to map such motion into vectors defined by the view direction of the virtual camera, as will be well known to persons skilled in the art.

A second, and generally less preferable, technique involves holding the virtual image 50 constant and moving video camera 45 (or the patient) until real image 55 matches virtual image 50.

Regardless of which technique is used, once virtual image 50 has been matched to real image 55, the position of the "virtual camera" (i.e., the location from which the virtual image appears to be seen) will be matched to the actual position of video camera 45.

Once virtual image 50 has been placed into proper registration with real image 55, image generator 30, video camera 45 and video mixing device 35 can be used to present the virtual and real images on display 40 in various presentation formats so as to facilitate a particular medical procedure. In particular, one can use image generator 30, video camera 45 and video mixing device 35 to superimpose a virtual image (generated from patient-specific 3-D computer model 15) against a real image (generated by video camera 45), with image generator 30 being directed to modify the virtual image so as to expose one or more of the virtual planning markers 25 present in patient-specific 3-D computer model 15, whereby the anatomy highlighted by virtual planning markers 25 will be brought quickly to the attention of the physician.

Figure 7:
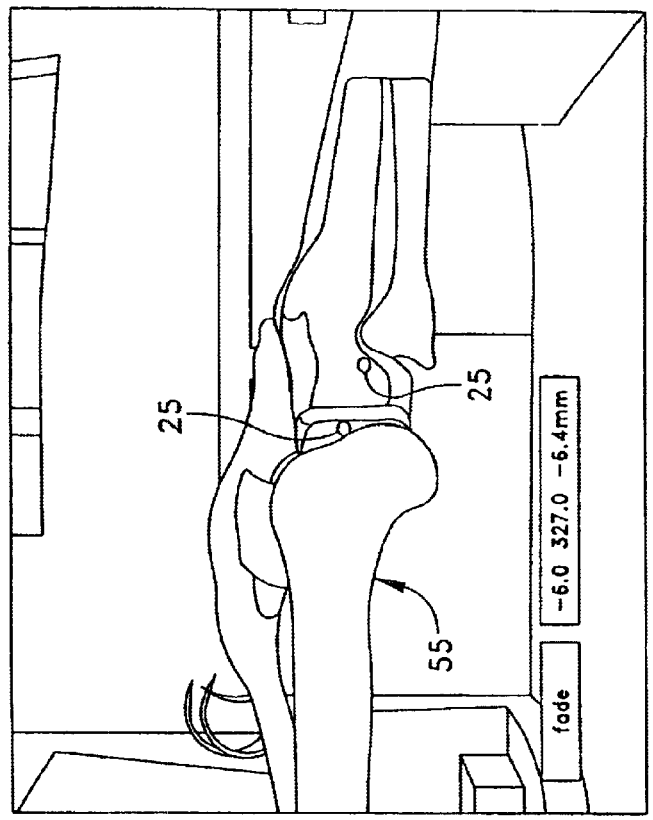
FIG. 7 is a view like that of FIG. 5, except that the virtual image generated from the 3-D computer model has been faded away to expose the virtual planning markers.
Figure 6:
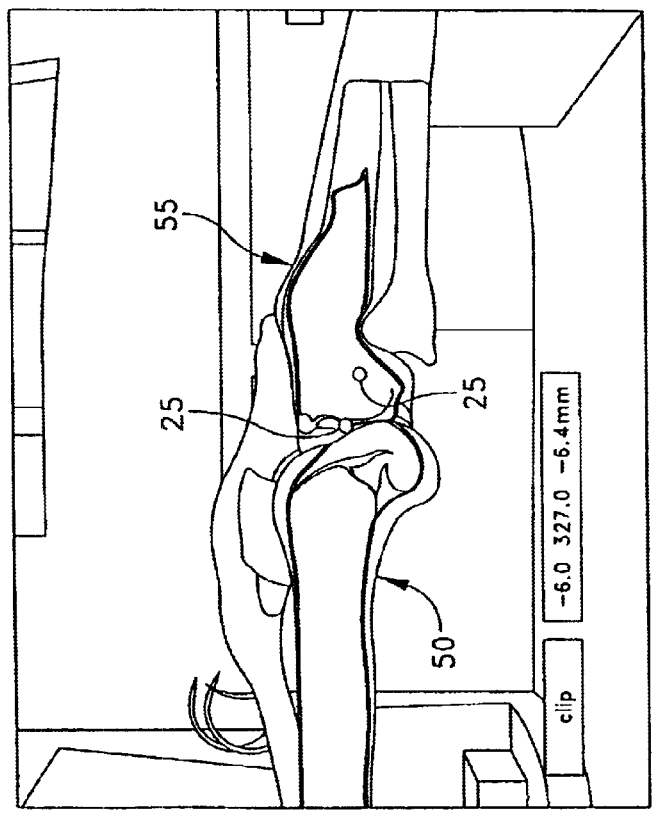
FIG. 6 is a view like that of FIG. 5, except that the virtual image generated from the 3-D computer model has been sliced away to expose the virtual planning markers.

In this respect it is to be appreciated that since virtual planning markers 25 will frequently be located within interior portions of the structure modeled by patient-specific 3-D computer model 15, exposing the otherwise-hidden virtual planning markers to view will involve rendering some or all of the virtual anatomical structure transparent or semi-transparent. This can be done either by (i) slicing away any portions of the virtual image required in order to expose virtual planning markers 25, whereby those virtual planning markers will be rendered visible against the background real image, in the manner shown in FIG. 6; or (ii) fading away some or all of the virtual image so as to expose such virtual planning markers against the real image, in the manner shown in FIG. 7. As a result, a physician can then conduct a medical procedure with the confidence of using real images generated by video camera 45, while having virtual planning markers 25 superimposed against the real image of the anatomical structure so as to help guide the procedure.

While the foregoing system constitutes a major improvement over the prior art, it has also been recognized that it can itself be improved upon significantly by adding camera tracking means to video camera 45.

More particularly, in many medical procedures, the position of video camera 45 may change on a fairly frequent basis. Since it is important for virtual image 50 (generated from patient-specific 3-D computer model 15) to remain in proper registration with real image 55 (obtained from video camera 45), it is necessary for the video-based surgical targeting system to reestablish proper correspondence between the two images each time the video camera moves. As noted above, this proper correspondence can be reestablished each time video camera 45 moves, by either (i) having the physician manually drag virtual image 50 into registration with real image 55, using a mouse or other data entry device attached to image generator 30, or (ii) having the system use a search algorithm to match the virtual image to the real image. While both of these procedures are generally capable (assuming that the anatomical structure remains stationary) of accurately yielding the desired image correspondence, each one suffers from a significant disadvantage. In the first case, requiring the physician to physically drag the virtual image into registration with the real image each time the video camera moves can be inconvenient where the video camera is moved about frequently. In the second case, it can take the system a substantial amount of time to solve for the correct image correspondence when using a search algorithm, even where high speed hardware is utilized. Even where speed is not a problem, automated search strategies of the type generally used are prone to errors through false matches.

Accordingly, it has been recognized that by putting a tracker on video camera 45, the position of the real camera can be continuously monitored, whereby each time the real camera moves, the position of the virtual camera can be correspondingly adjusted by image generator 30. In this way, the virtual image generated by image generator 30 can quickly and easily be maintained in registration with the real image, regardless of how often video camera 45 is moved.

Figure 8:
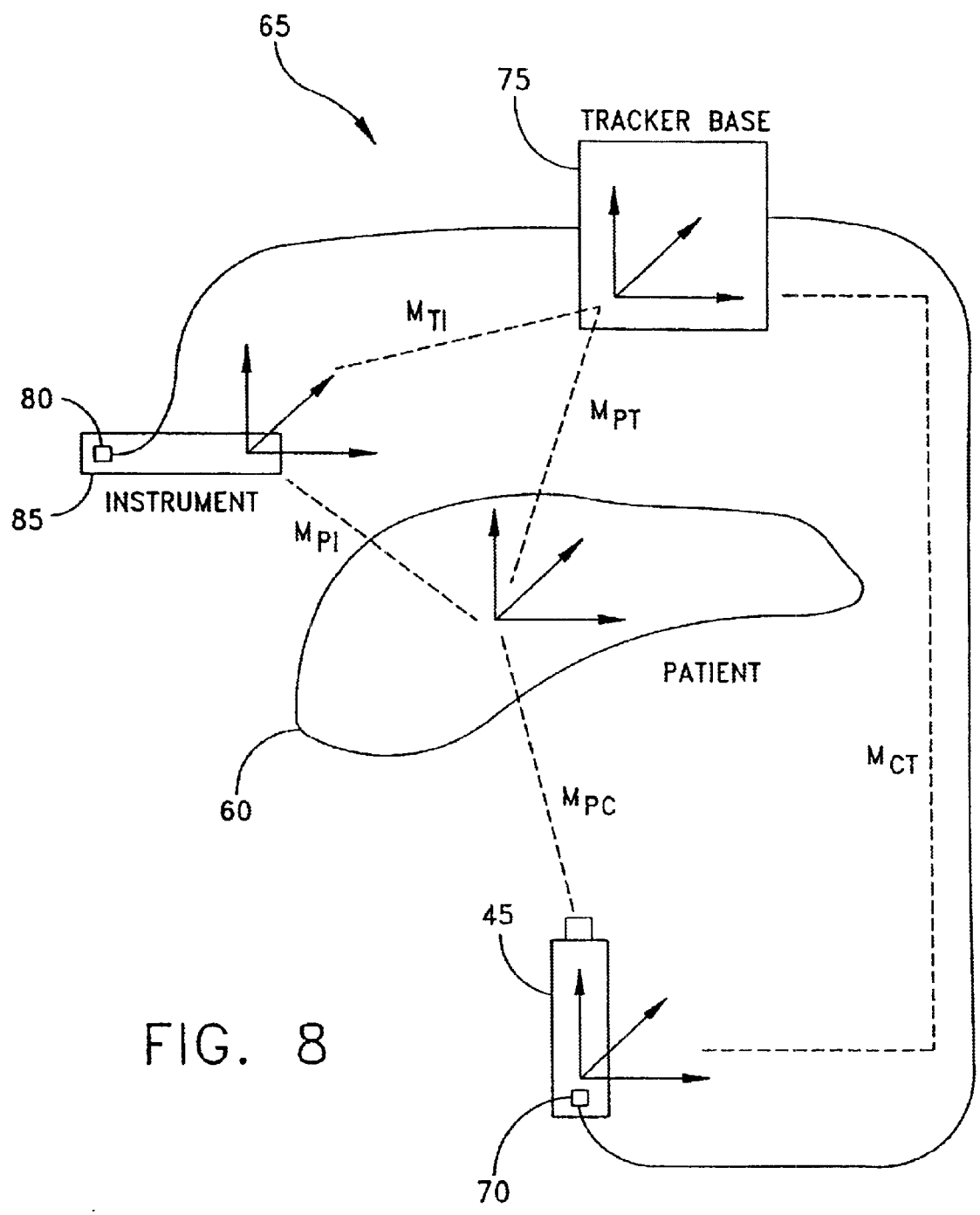
FIG. 8 is a schematic view showing the positional relationships between various elements of the video-based surgical targeting system and the patient's anatomical structure, as well as the positional relationship between an exemplary surgical instrument and the patient's anatomical structure.

More particularly, and looking now at FIG. 8, there is shown a video camera 45, an anatomical structure 60, and a tracker system 65. Tracker system 65 comprises a tracker 70 which is attached to video camera 45, and a tracker base 75 which defines the coordinate system of the tracker system.

In this setting, $M_{PC}$ can be considered to represent the matrix transformation from the patient's anatomical structure 60 to camera 45; $M_{CT}$ can be considered to represent the matrix transformation from camera 45 to tracker base 75; and $M_{PT}$ can be considered to represent the matrix transformation from anatomical structure 60 to tracker base 75.

$M_{CT}$ is known from the tracker system. Furthermore, once the virtual image generated by image generator 30 has been placed in registration with the real image generated by camera 45, the virtual camera position will be known relative to the virtual anatomical structure, and hence the real camera position will be known relative to die real anatomical structure. Thus, real matrix $M_{PC}$ will also be known. In addition, since $M_{CT}$ and $M_{PC}$ are then both known, it is possible to solve for $M_{PT}$. Accordingly, the position of anatomical structure 60 will then also be known within the relative coordinate system defined by the tracker system.

In view of the foregoing, the virtual image generated by image generator 30 can be quickly and easily maintained in registration with the real image, regardless of how often camera 45 is moved.

Furthermore, another tracker 80 can be positioned on a surgical instrument 85. In this case, tracker 80 will provide $M_{TI}$, where $M_{TI}$ represents the matrix transformation from tracker base 75 to instrument 85. Accordingly, once $M_{PT}$ and $M_{TI}$ are known, it is possible to solve for $M_{PI}$, where $M_{PI}$ represents the matrix transformation from the patient's anatomical structure 60 to instrument 85. With $M_{PI}$ known, it is then possible to track the position of surgical instrument 85 relative to anatomical structure 60. This is a very powerful tool, since it allows a virtual representation of surgical instrument 85 to be accurately added to the properly registered virtual and real images presented on display 40, i.e., it allows a virtual representation of instrument 85 to be shown in proper registration with a real image of anatomical structure 60 on display 40.

Figure 9:
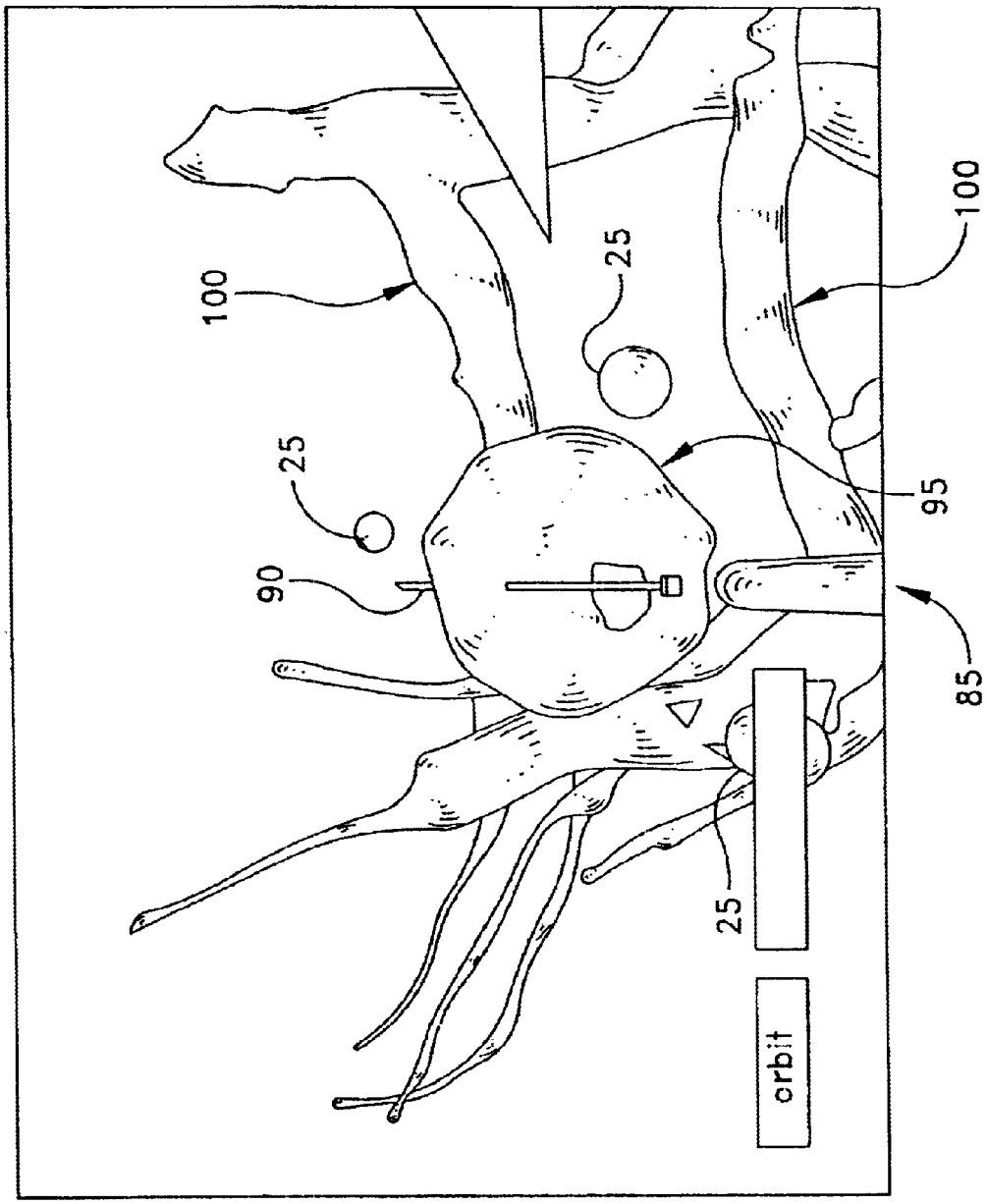
FIG. 9 is a virtual image generated from the 3-D computer model, showing a virtual "over the shoulder" view from the tip of a tracked surgical instrument.
Figure 10:
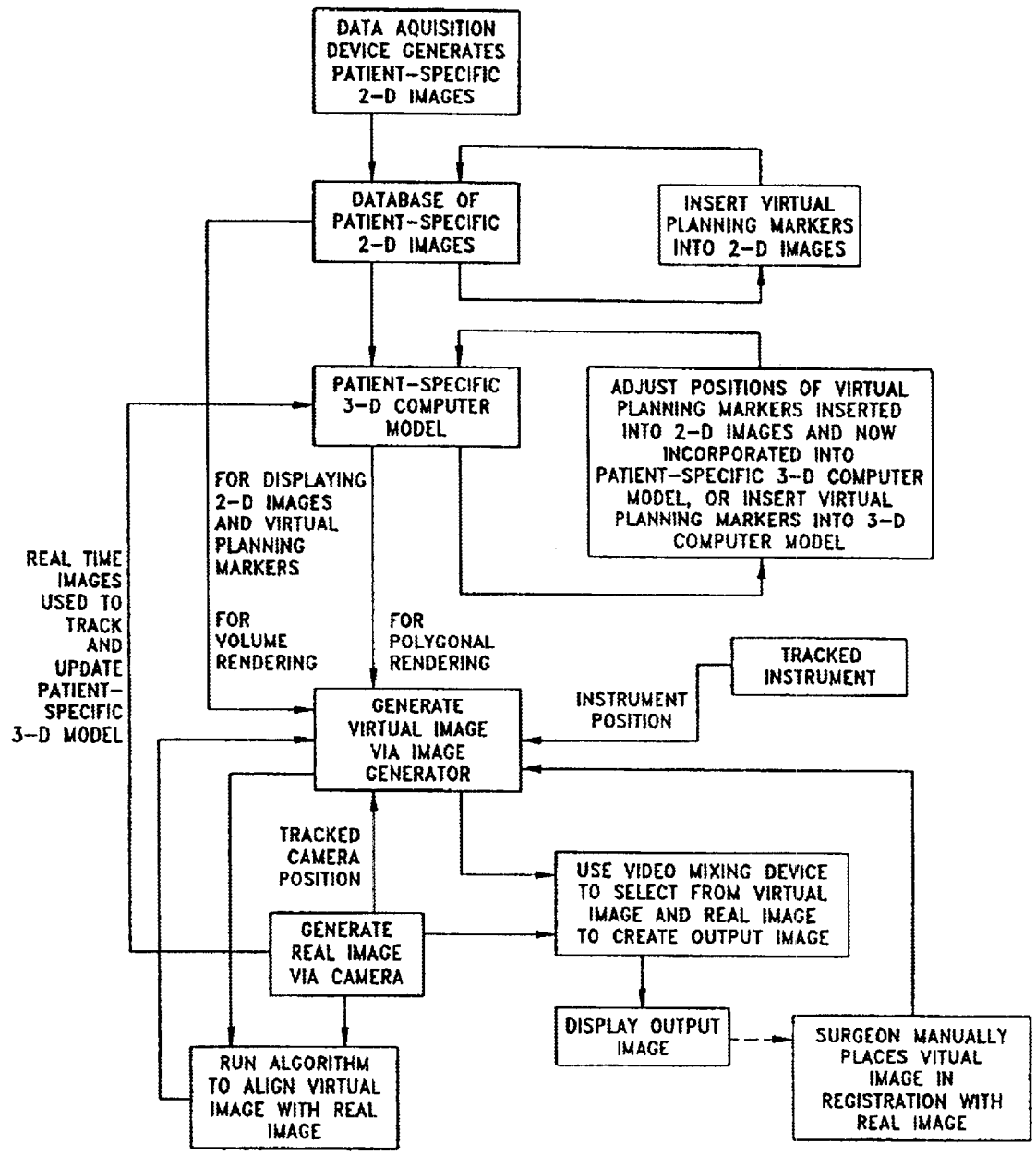
FIG. 10 is a flowchart illustrating one way of operating a video-based surgical targeting system formed in accordance with the present invention.

Furthermore, as the position of surgical instrument 85 is tracked relative to anatomical structure 60, it is also possible to provide a virtual image of surgical instrument 85 as that surgical instrument 85 moves through the anatomical structure, even when some or all of that instrument might be hidden from the view of video camera 45. For example, and looking now at FIG. 9, it is possible to generate a virtual "over the shoulder" view of the distal tip of surgical instrument 85 moving through anatomical structure 60, where that tip will be shown in proper correspondence to various structures, e.g. a tumor 95, vascular structures 100, etc. It is also possible to generate an additional virtual object 90 showing a line extended along the axis of the surgical instrument 85 so that the physician can see where the surgical instrument would go if moved further along its current trajectory. Of course, since the virtual image generated by the video-based surgical targeting system will then differ significantly from the real image generated by video camera 45, video mixing device 35 should be directed to totally suppress the real image generated by video camera 45 so that it will no longer be shown on display 40, in order to avoid confusing the physician.

Modifications Of The Preferred Embodiments

It is, of course, possible to modify the preferred embodiments disclosed above without departing from the scope of the present invention.

Thus, for example, while only one camera 45 has been disclosed above, it should be appreciated that two or more cameras 45 may be used. Furthermore, it should also be appreciated that camera 45 may comprise a video camera, or it may comprise an endoscope, or it may comprise some other type of real-time image capturing means, e.g. it may comprise an ultrasound device.

Additionally, it should be recognized that the system might be adapted so that patient-specific database 10 comprises non-2-D images, e.g. database 10 might comprise one or more images generated by a Cyberware 3-D scanner.

Alternatively, patient-specific 3-D computer model 15 might be omitted from the apparatus entirely. In this case, the virtual images could be generated from patient-specific database 10 by image generator 30 through the use of a volume rendering procedure of the sort well known in the art.

It is also anticipated that one could use a tracked surgical instrument 85 to determine the location of anatomical structure 60. This can be accomplished by using the tracked surgical instrument 85 to engage known fiducial points on the anatomical structure. Alternatively, a tracked surgical instrument 85 can be used to sample multiple surface points located on the anatomical structure and then use a data matching procedure to correlate the sampled points with either patient-specific database 10 or patient-specific 3-D computer model 15. By way of example, a least squares fit might be used to correlate the sampled points with the 3-D computer model.

Also, it should be appreciated that the video-based targeting system could be used to target objects in non-medical applications, e.g. it could be used to target objects concealed within the interior of complex machines, or objects (e.g. a conduit) concealed beneath surface of a structure (e.g. the floor of a building).

Furthermore, it is possible to place tracking means directly on the patient so as to track the position of the patients anatomical structure.

Still other changes will be obvious to a person skilled in the art.

Advantages Of The Present Invention

Numerous advantages are obtained through the use of the present invention.

For one thing, a surgical targeting system is provided to facilitate locating a particular anatomical structure during a medical procedure.

For another thing, a video-based surgical targeting system is provided to facilitate locating a particular anatomical structure during a medical procedure.

And a video-based surgical targeting system is provided which permits a series of patient-specific 2-D images (obtained by scanning patient anatomy using one or more scanning devices of the type described above) to be assembled into a 3-D computer model of the patient's scanned structure.

Also, a video-based surgical targeting system is provided which allows a physician to view the aforementioned patient-specific 2-D images on a display in any desired access sequence.

Furthermore, a video-based surgical targeting system is provided which allows a physician to assemble a series of patient-specific 2-D images into a patient-specific database, and then to generate virtual images from the aforementioned patient-specific database, as seen from any desired virtual camera position, for viewing on a display.

And a video-based surgical targeting system is provided which allows a physician to generate virtual images from the aforementioned 3-D computer model, as seen from any desired virtual camera position, for viewing on a display.

In addition, a video-based surgical targeting system is provided which permits a physician to place virtual planning markers about any sites of interest while viewing one or more of the aforementioned patient-specific 2-D images, with those virtual planning markers then being incorporated into the 3-D computer model, whereby those virtual planning markers can be displayed in their appropriate 3-D positions when generating virtual images of the 3-D computer model.

And a video-based surgical targeting system is provided which permits a physician to place virtual planning markers about any sites of interest while viewing virtual images of the 3-D computer model, with those virtual planning markers then being incorporated into the 3-D computer model, whereby those virtual planning markers can be displayed in their appropriate positions when subsequently generating virtual images of the 3-D computer model.

And a video-based surgical targeting system is provided which permits a physician to place virtual planning markers about any sites of interest while viewing virtual images of the 3-D computer model, with those virtual planning markers then being incorporated into the 3-D computer model and into the database of 2-D images, whereby those virtual planning markers can be displayed in their appropriate positions when subsequently generating virtual images of the 3-D computer model or when subsequently displaying 2-D images from the patient-specific database.

For another thing, a video-based surgical targeting system is provided which permits a real image obtained by a real-time imaging device (e.g. a video camera) to be displayed to a physician, and which permits a virtual image generated from the 3-D computer model to be displayed to a physician, according to the directive of the physician.

And a video-based surgical targeting system is provided which permits a real image obtained by a real-time imaging device (e.g. a video camera) to be appropriately merged with a corresponding virtual image generated from the 3-D computer model.

Also, a video-based surgical targeting system is provided which permits a real image obtained by a real-time imaging device (e.g. a video camera) to be appropriately merged with a corresponding virtual image generated from the 3-D computer model, whereby the two images will be in registration with one another.

Furthermore, a video-based surgical targeting system is provided which permits a real image obtained by a real-time imaging device (e.g. a video camera) to be merged with a corresponding virtual image generated from the 3-D computer model, whereby the two images will be in registration with one another, and whereby the physician can choose to display either one of the two images exclusive of the other, or a composite of both images simultaneously.

And a video-based surgical targeting system is provided which permits a real image obtained by a real-time imaging device (e.g. a video camera) to be merged with a corresponding virtual image generated from the 3-D computer model, whereby the two images will be simultaneously displayed in registration with one another, and whereby the physician can modify the virtual image generated from the 3-D computer model as needed, by clipping or fading, so as to expose the virtual planning markers to view, with the virtual planning markers being superimposed on the real image generated by the real-time imaging device.

And a video-based surgical targeting system is provided which permits a real image generated by a real-time imaging device (e.g. a video camera) to be merged with a corresponding virtual image generated from the 3-D computer model, whereby the two images will be simultaneously displayed in registration with one another, and whereby the physician can modify the virtual image generated from the 3-D computer model so as to expose only the virtual planning markers to view, with the virtual planning markers being superimposed on the real image generated by the real-time imaging device.

Moreover, a video-based surgical targeting system is provided which permits a real image obtained by a real-time imaging device (e.g. a video camera) to be merged with a corresponding virtual image generated from the 3-D computer model, whereby the two images will be simultaneously displayed in registration with one another, and whereby this registration will be automatically maintained even as the real-time imaging device is moved about relative to the anatomical site, with the virtual image being automatically generated so as to follow the real image.

And a video-based surgical targeting system is provided which permits a real image obtained by a real-time imaging device (e.g. a video camera) to be merged with a corresponding virtual image generated from the 3-D computer model, whereby the two images will be simultaneously displayed in registration with one another, and whereby this registration will be automatically maintained through the use of a computerized position and orientation tracker connected to the imaging device even as the real-time imaging device is moved about relative to the anatomical site, with the virtual image being automatically generated so as to follow the real image.

Also, a video-based surgical targeting system is provided which permits a real image obtained by a real-time imaging device (e.g. a video camera) to be merged with a corresponding virtual image generated from the 3-D computer model, whereby the two images will be simultaneously displayed in registration with one another, and whereby this registration will be automatically maintained through the use of a computer search algorithm based on the real image and the virtual image even as the real-time imaging device is moved about relative to the anatomical site, with the virtual image being automatically generated so as to follow the real image.

And a video-based surgical targeting system is provided which permits a real image obtained by a real-time imaging device (e.g. a video camera) to be merged with a corresponding virtual image generated from the 3-D computer model, whereby the two images will be simultaneously displayed in registration with one another, and whereby a surgical instrument can be tracked along with the real-time imaging device in order that the surgical instrument can be guided about the anatomical site using the virtual image generated from the 3-D computer model.

In addition, a video-based surgical targeting system is provided which permits a virtual image to be generated from the 3-D computer model, and further wherein this virtual image can correspond to an "over the shoulder" view of the working tip of a surgical instrument located at the anatomical site.

And an improved method for locating anatomical structures during a medical procedure is provided.

What is claimed is:

1. A video-based surgical targeting system comprising:
   a patient-specific database comprising a plurality of 2-D images of the anatomical structure of a patient;
   a patient-specific 3-D computer model of said anatomical structure of said patient, said patient-specific 3-D computer model being assembled from said plurality of 2-D images contained in said patient-specific database;
   marker placement means for (i) inserting virtual planning markers into said 2-D images contained in said patient-specific database, and/or (ii) adjusting the positions of virtual planning markers inserted into said 2-D images contained in said patient-specific database and thereafter incorporated into said patient-specific 3-D computer model, or inserting virtual planning markers into said 3-D computer model;
   an image generator for generating a virtual image of the anatomical structure modeled by said patient-specific 3-D computer model;
   real-time image generating means for generating a real image of the anatomical structure of a patient;
   video mixing means for mixing said virtual image and said real image into an output image, whereby said output image may comprise either one of the two images exclusive of the other, or a composite of both images; and
   display means for displaying said output image.

2. A video-based surgical targeting system according to claim 1 wherein said system further comprises registration means for placing said virtual image in registration with said real image.

3. A video-based surgical targeting system according to claim 2 wherein said registration means include means for manually aligning said virtual image with said real image.

4. A video-based surgical targeting system according to claim 2 wherein said registration means include means for automatically aligning said virtual image with said real image.

5. A video-based surgical tracking system according to claim 4 wherein said registration means are adapted to use said real image to track and update said patient-specific 3-D computer model.

6. A video-based surgical targeting system according to claim 2 wherein said registration means include tracking means for tracking the position of said real-time image generating means.

7. A video-based surgical targeting system according to claim 2 wherein said system further comprises instrument tracking means for tracking the position of a surgical instrument.

8. A video-based surgical targeting system according to claim 2 wherein said system further comprises patient tracking means for tracking the position of said anatomical structure.

9. A video-based surgical targeting system according to claim 2 wherein said registration means comprise a surgical instrument and tracking means for tracking the position of said surgical instrument, and further wherein said registration means comprise means for effecting registration when said surgical instrument engages known fiducial marks located on said anatomical structure.

10. A video-based surgical tracking system according to claim 2 wherein said registration means comprise a surgical instrument and tracking means for tracking the position of said surgical instrument, and further wherein said registration means comprise means for effecting registration when said surgical instrument samples multiple surface points located on said anatomical structure, with said means for effecting registration using a data matching procedure to correlate said sampled points with said patient-specific database.

11. A video-based surgical targeting system according to claim 1 wherein said real-time image generating means comprise a video camera.

12. A video-based surgical targeting system according to claim 1 wherein said real-time image generating means comprise an endoscope.

13. A video-based surgical targeting system according to claim 1 wherein said real-time image generating means comprise an ultrasound device.

14. A video-based surgical targeting system according to claim 1 wherein said patient-specific 3-D computer model is constructed out of one or more polygonal models.

15. A video-based surgical targeting system according to claim 1 wherein said image generator generates said virtual image by a polygonal rendering process.

16. A video-based surgical targeting system comprising:
    a patient-specific database comprising a plurality of 2-D images of the anatomical structure of a patient;
    marker placement means for inserting virtual planning markers into said 2-D images contained in said patient-specific database;
    an image generator for generating a virtual image of the anatomical structure represented by said plurality of 2-D images contained in said patient-specific database;
    real-time image generating means for generating a real image of the anatomical structure of a patient;
    video mixing means for mixing said virtual image and said real image into an output image, whereby said output image may comprise either one of the two images exclusive of the other, or a composite of both images; and
    display means for displaying said output image.

17. A video-based surgical targeting system according to claim 16 wherein said image generator generates said virtual image by a volume rendering process.

18. A video-based surgical targeting system comprising:
    a patient-specific database comprising a plurality of images of the anatomical structure of a patient;
    a patient-specific 3-D computer model of said anatomical structure of said patient, said patient-specific 3-D computer model being assembled from said plurality of images contained in said patient-specific database;
    marker placement means for (i) inserting virtual planning markers into said images contained in said patient-specific database, and/or (ii) adjusting the positions of virtual planning markers inserted into said images contained in said patient-specific database and thereafter incorporated into said patient-specific 3-D computer model, or inserting virtual planning markers into said 3-D computer model;
    an image generator for generating a virtual image of the anatomical structure modeled by said patient-specific 3-D computer model;
    real-time image generating means for generating a real image of the anatomical structure of a patient;

video mixing means for mixing said virtual image and said real image into an output image, whereby said output image may comprise either one of the two images exclusive of the other, or a composite of both images; and display means for displaying said output image.

19. A video-based surgical targeting system comprising:

a patient-specific database comprising a plurality of 2-D images of the anatomical structure of a patient;

marker placement means for inserting virtual planning markers into said 2-D images contained in said patient-specific database;

an image generator for generating a virtual image of the anatomical structure defined by said patient-specific database;

real-time image generating means for generating a real image of the anatomical structure of a patient, said real-time image generating means being adapted so as to dynamically update said patient-specific database with said real image;

video mixing means for mixing said virtual image and said real image into an output image, whereby said output image may comprise either one of the two images exclusive of the other, or a composite of both images; and display means for displaying said output image.

20. A method for targeting an anatomical structure, said method comprising the steps of:

(1) providing a video-based surgical targeting system comprising:

a patient-specific database comprising a plurality of 2-D images of the anatomical structure of a patient;

a patient-specific 3-D computer model of said anatomical structure of said patient, said patient-specific 3-D computer model being assembled from said plurality of 2-D images contained in said patient-specific database;

marker placement means for (i) inserting virtual planning markers into said 2-D images contained in said patient-specific database, and/or (ii) adjusting the positions of virtual planning markers inserted into said 2-D images contained in said patient-specific database and thereafter incorporated into said patient-specific 3-D computer model, or inserting virtual planning markers into said 3-D computer model;

an image generator for generating a virtual image of the anatomical structure modeled by said patient-specific 3-D computer model;

real-time image generating means for generating a real image of the anatomical structure of a patient;

video mixing means for mixing said virtual image and said real image into an output image, whereby said output image may comprise either one of the two images exclusive of the other, or a composite of both images; and display means for displaying said output image;

(2) inserting a visual planning marker into a 2-D image contained in said patient-specific database;

(3) generating a virtual image of the anatomical structure defined by said patient-specific 3-D model, and generating a real image of the anatomical structure of a patient;

(4) mixing said virtual image and said real image into an output image, whereby said output image comprises a composite of both images, and displaying said output image on said display means, wherein said virtual image and said real image are mixed so that said visual planning marker is exposed to view so as to be superimposed against said real image.

21. A method according to claim 20 wherein said virtual image and said real image are mixed so as to be in registration with one another.

22. A method according to claim 21 wherein said video-based surgical targeting system comprises means for maintaining said virtual image and said real image in registration with one another even when said real-time image generating means move relative to said anatomical structure.

23. A method for targeting an anatomical structure, said method comprising the steps of:

(1) providing a video-based surgical targeting system comprising:

a patient-specific database comprising a plurality of 2-D images of the anatomical structure of a patient;

marker placement means for inserting virtual planning markers into said 2-D images contained in said patient-specific database;

an image generator for generating a virtual image of the anatomical structure represented by said plurality of 2-D images contained in said patient-specific database;

real-time image generating means for generating a real image of the anatomical structure of a patient;

video mixing means for mixing said virtual image and said real image into an output image, whereby said output image may comprise either one of the two images exclusive of the other, or a composite of both images; and display means for displaying said output image;

(2) inserting a visual planning marker into a 2-D image contained in said patient-specific database;

(3) generating a virtual image of the anatomical structure represented by said plurality of 2-D images contained in said patient-specific database, and generating a real image of the anatomical structure of a patient; and (4) mixing said virtual image and said real image into an output image, whereby said output image comprises a composite of both images, and displaying said output image on said display means, wherein said virtual image and said real image are mixed so that said visual planning marker is exposed to view so as to be superimposed against said real image.

24. A method for targeting an anatomical structure, said method comprising the steps of:

(1) providing a video-based surgical targeting system comprising:

a patient-specific database comprising a plurality of images of the anatomical structure of a patient;

a patient-specific 3-D computer model of said anatomical structure of said patient, said patient-specific 3-D computer model being assembled from said plurality of images contained in said patient-specific database;

marker placement means for (i) inserting virtual planning markers into said images contained in said patient-specific database, and/or (ii) adjusting the positions of virtual planning markers inserted into said images contained in said patient-specific database and thereafter incorporated into said patient-specific 3-D computer model, or inserting virtual planning markers into said 3-D computer model;

an image generator for generating a virtual image of the anatomical structure modeled by said patient-specific 3-D computer model;

real-time image generating means for generating a real image of the anatomical structure of a patient;

video mixing means for mixing said virtual image and said real image into an output image, whereby said output image may comprise either one of the two images exclusive of the other, or a composite of both images; and display means for displaying said output image;

(2) inserting a visual planning marker into an image contained in said patient-specific database;

(3) generating a virtual image of the anatomical structure defined by said patient-specific 3-D model, and generating a real image of the anatomical structure of a patient; and (4) mixing said virtual image and said real image into an output image, whereby said output image comprises a composite of both images, and displaying said output image on said display means, wherein said virtual image and said real image are mixed so that said visual planning marker is exposed to view so as to be superimposed against said real image.

25. A method for targeting an anatomical structure, said method comprising the steps of:

(1) providing a video-based surgical targeting system comprising:

a patient-specific database comprising a plurality of 2-D images of the anatomical structure of a patient;

marker placement means for inserting virtual planning markers into said 2-D images contained in said database;

an image generator for generating a virtual image of the anatomical structure defined by said patient-specific database;

real-time image generating means for generating a real image of the anatomical structure of a patient, said real-time image generating means being adapted so as to dynamically update said patient-specific database with said real image;

video mixing means for mixing said virtual image and said real image into an output image, whereby said output image may comprise either one of the two images exclusive of the other, or a composite of both images; and display means for displaying said output image;

(2) inserting a visual planning marker into a 2-D image contained in said patient-specific database;

(3) generating a virtual image of the anatomical structure defined by said patient-specific 3-D model, and generating a real image of the anatomical structure of a patient; and (4) mixing said virtual image and said real image into an output image, whereby said output image comprises a composite of both images, and displaying said output image on said display means, wherein said virtual image and said real image are mixed so that said visual planning marker is exposed to view so as to be superimposed against said real image.

\* \* \* \* \*